United States Patent [19]

Weeks

[11] Patent Number: Plant 6,862

[45] Date of Patent: Jun. 20, 1989

[54] ROSE PLANT NAMED 'BACARDI'

[76] Inventor: O. L. Weeks, 12610 Central Ave., Suite 76, Chino, Calif. 91710

[21] Appl. No.: 159,530

[22] Filed: Feb. 9, 1988

[51] Int. Cl.[4] ..... A01H 5/00

[52] U.S. Cl. ..... Plt./11

[58] Field of Search ..... Plt./11

*Primary Examiner*—James R. Feyrer

*Attorney, Agent, or Firm*—Vincent G. Gioia

[57] ABSTRACT

A new coral pink grandiflora rose.

1 Drawing Sheet

1

The present invention relates to a new and distinct variety of rose plant of the Grandiflora rose class, which was originated by my crossing as seed parent the variety known as "October" (U.S. Plant Pat. No. 4,768) and a pollen parent an unnamed, unpatented seedling of my creation. The denomination of this new rose is "Bacardi".

Among the novel characteristics possessed by this new variety which distinguish it from its parents and all other varieties of which I am aware are its coral pink flowers of good exhibition form which open well and are long lasting on the plant. Asexual reproduction by budding of the new variety as performed in San Bernardino County, Calif., shows that the foregoing and other distinguishing characteristics come true to form and are established and transmitted through succeeding propagations.

The seed parent, "October", is a clear, smooth orange color whereas the new seedling has flowers of reddish coral. The seed parent is a hybrid tea with typical hybrid tea buds and open blooms. The flowers of the seed parent are larger than the flowers of the new seedling. The seed parent plant is less compact and not as tall as the new seedling and has darker, glossier foliage.

Flowers on the pollen parent, an unnamed seedling, are orange-red in color and of deeper shading than the new seedling and are also larger than those of the new seedling.

The pleasant color of the blooms and the symmetry of plant habit of this new variety makes it an asset to the beauty and harmony of the gardenscape. Dense, attractive foliage on a well-contained and disciplined plant and other additional desirable features make it a welcome and useful addition to the garden between periods of color. The exhibition form of bud and partially open bloom are also desirable traits.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "43D" is plate 43D of The Royal Horticultural Society Colour Chart.

Parentage: Seedling.

*Seed parent.*—"October".

2

*Pollen Parent.*—Unnamed seedling.

Class: Grandiflora.

The following observations are made of specimens grown outdoors in San Bernardino County, Calif., during the month of October.

FLOWER

Blooming habit: Recurrent.

A. Bud:

(1) *Size.*—Small.

(2) *Form.*—Pointed.

(3) *Color.*—As sepals divide, bud color is near 43D and near 43C at petal edge with yellow tinting toward point of petal attachment.

(4) *Sepals.*—Yellow green near 144B extending beyond tip of unopened bud, slightly foliated.

(5) *Peduncle.*—Length — long. Aspect — regular with numerous small prickles. Strength — erect. Color — near 144B.

B. Bloom:

(1) *Size.*—Average size when fully expanded — about 3¼ inches.

(2) *Borne.*—Singly, one to a stem and several together in small sprays.

(3) *Form.*—High centered until fully open. Outer petals reflex and quill to points; inner petals roll under.

(4) Petalage.—Number of petals under normal conditions — about 40 to 45.

(5) *Color.*—After sepals fall and petals unfurl, flower coloring varies from near 48A at its deepest tonality on petals top surfaces and at petal apices to near Empire Rose 48D at its lightest tonality at the petal undersurfaces. Flowers may also show mottling and weathering markings which appear as spots of near 48A coloring. As flowers open fully and age, petals brighten to near 49D but the ends of outer petals and apices still retain near 48A markings. Thus, coloring of petal top surface of outer petals appears deeper toned than coloring of the top surfaces of inner petals, especially at petal tips and edges. After several days petal tips fade to light coral pink near 38D and retain a weathered mottling or spotting effect.

C. Petals:

(1) *Texture.*—Thick.

(2) *Appearance.*—Inside and outside satiny.

(3) *Form.*—Broad, fan shaped, ovoid.

(4) *Arrangement.*—Regularly arranged.

(5) *Petaloids in center.*—Few.
(6) *Persistence.*—Petals persist.
(7) *Fragrance.*—Slight.
(8) *Lasting quality.*—Very long lasting quality on plant and long lasting as cut flower.

REPRODUCTIVE ORGANS

A. Stamens, filaments and anthers:
*Arrangement and color.*—Irregularly arranged around styles. Anthers — yellow orange with brownish cast. Color — filaments yellow green with reddish cast at center.

B. Pollen:
*Color.*—Near 17A with brownish cast.

C. Styles: Even, medium length, uneven, bunched.

D. Stigmas:
*Color.*—Yellow.

E. Hips: Slightly globular, small, near yellow-green 144B; seeds do not protrude.

PLANT

A. Form: Compact, slightly spreading.

B. Growth: Vigorous.
*Height attained.*—About 3 feet.

C. Foliage: Compound 5 leaflets.
(1) *Size.*—Small to medium.
(2) *Quantity.*—Abundant.
(3) *Color.*—New foliage: Upper side — reddish purple. Under side — near 148B with reddish overlay. Old foliage: Upper side — near 147A with reddish serration. Under side — near to 147C with brushed copper reddish tint.
(4) *Shape.*—Elongated oval, pointed.
(5) *Texture.*—Upper side is semiglossy; under side is matte.
(6) *Edge.*—Serrate.
(7) *Serration.*—Ordinary.
(8) *Leaf stem.*—Color — near to 147C.
(9) *Stipules.*—Medium length, smooth.
(10) *Resistance to Disease.*—Blackspot — Average. Mildew — Average. Rust — None.

D. Wood:
(1) *New wood.*—Color — near 146C. Bark — smooth.
(2) *Old wood.*—Color — near 146C. Bark — smooth.

E. Thorns:
(1) *Thorns.*—Quantity (main stalk) — ordinary. On laterals from stalks — few. Form — long, thin, straight, flat base. Length — short. Color — light green to tan. Position — irregular.
(2) Prickles.—Numerous.

F. Winter Hardiness: Average, needs protection in severe climates.

I claim:

1. A new and distinct variety of rose plant of the grandiflora rose class and all parts thereof, substantially as shown and described, characterized particularly by coral pink flowers which open well and are long lasting on the plant.

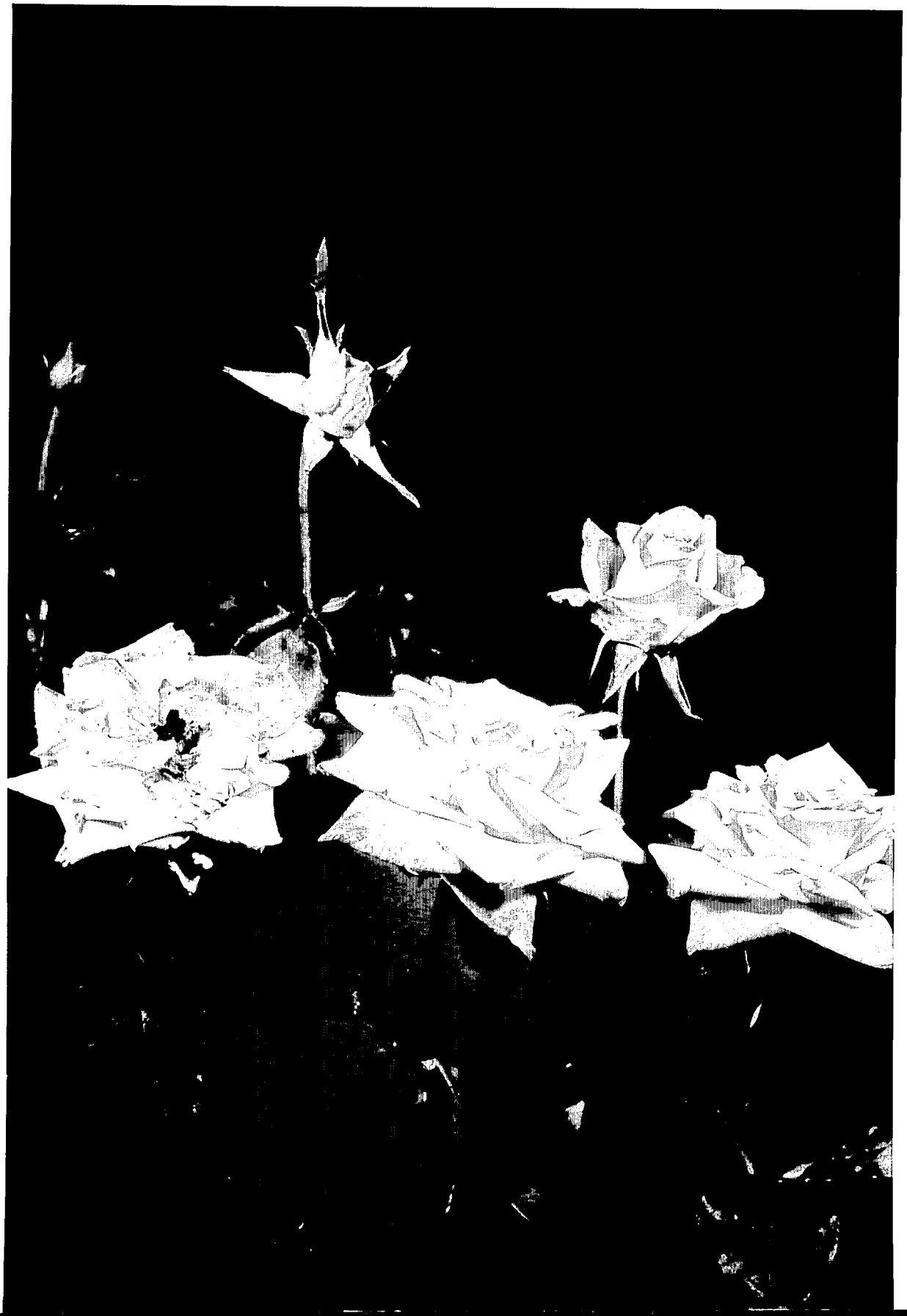

* * * * *